(12) United States Patent
Hakimimehr et al.

(10) Patent No.: US 8,529,941 B2
(45) Date of Patent: Sep. 10, 2013

(54) FREE-STANDING BIODEGRADABLE PATCH

(75) Inventors: Dorna Hakimimehr, Santa Rosa, CA (US); Raoul Bonan, Mirabel (CA)

(73) Assignee: Bioinspire Technologies, Inc., Palo Alto, CA (US)

( * ) Notice: Subject to any disclaimer, the term of this patent is extended or adjusted under 35 U.S.C. 154(b) by 257 days.

(21) Appl. No.: 12/885,322

(22) Filed: Sep. 17, 2010

(65) Prior Publication Data

US 2011/0071499 A1   Mar. 24, 2011

Related U.S. Application Data

(60) Provisional application No. 61/243,979, filed on Sep. 18, 2009.

(51) Int. Cl.
*A61K 9/70* (2006.01)
(52) U.S. Cl.
USPC .......................................... 424/443; 424/445
(58) Field of Classification Search
None
See application file for complete search history.

(56) References Cited

U.S. PATENT DOCUMENTS

| | | | |
|---|---|---|---|
| 4,298,598 A | 11/1981 | Schwarz et al. | |
| 4,362,567 A | 12/1982 | Schwarz et al. | |
| 4,377,572 A | 3/1983 | Schwarz et al. | |
| 4,453,939 A | 6/1984 | Zimmerman et al. | |
| 4,548,736 A | 10/1985 | Müller et al. | |
| 4,560,374 A | 12/1985 | Hammerslag | |
| 4,577,631 A | 3/1986 | Kreamer | |
| 5,092,841 A | 3/1992 | Spears | |
| 5,100,429 A | 3/1992 | Sinofsky et al. | |
| 5,213,580 A | 5/1993 | Slepian et al. | |
| 5,223,420 A * | 6/1993 | Rabaud et al. | 424/425 |
| 5,487,897 A | 1/1996 | Polson et al. | |
| 5,510,077 A | 4/1996 | Dinh et al. | |
| 5,575,815 A | 11/1996 | Slepian et al. | |
| 5,591,224 A | 1/1997 | Schwartz et al. | |

(Continued)

FOREIGN PATENT DOCUMENTS

| | | |
|---|---|---|
| WO | WO 92/13495 | 8/1992 |
| WO | WO 96/22115 | 7/1996 |

(Continued)

OTHER PUBLICATIONS

Atrah, H.I., Fibrin Glue, BMJ 308: 933 (Apr. 9, 1994).

(Continued)

*Primary Examiner* — Anand Desai
*Assistant Examiner* — Melissa Mercier
(74) *Attorney, Agent, or Firm* — Foley & Lardner LLP; Nicola A. Pisano; Christopher C. Bolten

(57) ABSTRACT

Methods and apparatus for a free-standing biodegradable patch suitable for medical applications, especially intravascular, minimally-invasive and intraoperative surgical applications are provided, wherein the patch comprises a free-standing film or device having a mixture of a solid fibrinogen component and a solid thrombin component that, when exposed to an aqueous environment, undergoes polymerization to form fibrin. In alternative embodiments the patch may comprise a solid fibrinogen component, with or without an inorganic calcium salt component. The patch may take a non-adherent form during delivery to a target location within a vessel or tissue, and thereafter may be activated to adhere to vessel wall or tissue, and may include a number of additives, including materials to improve the mechanical properties of the patch, or one or more therapeutic or contrast agents.

16 Claims, 3 Drawing Sheets

(56) References Cited

U.S. PATENT DOCUMENTS

| | | | |
|---|---|---|---|
| 5,591,227 A | 1/1997 | Dinh et al. | |
| 5,599,307 A | 2/1997 | Bacher et al. | |
| 5,634,936 A | 6/1997 | Linden et al. | |
| 5,634,946 A | 6/1997 | Slepian | |
| 5,651,982 A | 7/1997 | Marx | |
| 5,693,085 A | 12/1997 | Buirge et al. | |
| 5,733,563 A | 3/1998 | Fortier | |
| 5,762,625 A | 6/1998 | Igaki | |
| 5,792,106 A | 8/1998 | Mische | |
| 5,899,917 A | 5/1999 | Edwards et al. | |
| 5,942,278 A | 8/1999 | Hagedorn et al. | |
| 6,039,757 A | 3/2000 | Edwards et al. | |
| 6,054,122 A | 4/2000 | MacPhee et al. | |
| 6,177,126 B1 | 1/2001 | Hagedorn et al. | |
| 6,290,729 B1 | 9/2001 | Slepian et al. | |
| 6,312,457 B1 | 11/2001 | DiMatteo et al. | |
| 6,893,431 B2 | 5/2005 | Naimark et al. | |
| 7,044,982 B2 | 5/2006 | Milbocker | |
| 7,057,019 B2 | 6/2006 | Pathak | |
| 7,098,315 B2 | 8/2006 | Schaufler | |
| 7,399,483 B2 | 7/2008 | Stimmeder | |
| 7,402,172 B2 | 7/2008 | Chin et al. | |
| 7,442,397 B2 | 10/2008 | Zhang | |
| 7,481,788 B2 | 1/2009 | Naimark et al. | |
| 7,572,769 B2 | 8/2009 | Rapp et al. | |
| 7,597,882 B2 | 10/2009 | Pathak et al. | |
| 7,662,409 B2 | 2/2010 | Masters | |
| 7,727,547 B2 | 6/2010 | Fortune et al. | |
| 7,780,980 B2 | 8/2010 | Sawhney | |
| 2005/0032205 A1 | 2/2005 | Smith et al. | |
| 2005/0277577 A1* | 12/2005 | Hunter et al. | 514/2 |
| 2009/0098176 A1 | 4/2009 | Helmus et al. | |
| 2009/0216264 A1 | 8/2009 | Friedman et al. | |
| 2009/0311338 A1 | 12/2009 | Pathak et al. | |
| 2012/0209319 A1* | 8/2012 | Bianco-Peled et al. | 606/213 |

FOREIGN PATENT DOCUMENTS

| | | | |
|---|---|---|---|
| WO | WO9715188 | * | 1/1997 |
| WO | WO 97/37694 | | 10/1997 |
| WO | WO 02/058750 A2 | | 8/2002 |

OTHER PUBLICATIONS

Cederholm-Williams, S.A., Fibrin Glue, BMJ 308: 1570 (Jun. 11, 1994).

Thompson et al., Fibrin Glue: A Review of its Preparation, Efficacy, and Adverse Effects as a Topical Hemostat, Drug Intelligence & Clinical Pharmacy: vol. 22, No. 12, pp. 946-952 (1988).

International Search Report for PCT/US2010/049114, 4 pages, mailed Mar. 3, 2011.

Response to Written Opinion for PCT/US2010/049114, filed Jun. 2, 2011.

Written Opinion for PCT/US2010/049114, 5 pages, mailed Mar. 3, 2011.

* cited by examiner

FREE-STANDING BIODEGRADABLE PATCH

I. CROSS-REFERENCE TO RELATED APPLICATION

This application claims the benefit of priority of U.S. provisional patent application Ser. No. 61/243,979, filed Sep. 18, 2009, the content of which are incorporated herein by reference in its entirety.

II. FIELD OF THE INVENTION

The present invention relates generally to patches for vessel and organ repair and drug delivery, including free-standing biodegradable patches.

III. BACKGROUND OF THE INVENTION

As some of the leading causes of death in the United States, cardiovascular diseases affect millions. Some diseases result in the weakening of blood vessels, while others result from the stenosis of a blood vessel. Stents have been used to provide support and drug-delivery to these blood vessels, but stent implantation carries a number of risks. For example, blood clots may develop at the site of the stent as the body rejects the foreign object, or the stent itself may migrate or fracture. As such, alternative methods of providing support to weakened blood vessels may be desirable.

Another prominent cause of cardiac ischemia and stroke is the occurrence of vulnerable plaque deposits that can accumulate within an individual's vasculature. Such plaque deposits result when a lipid pool forms beneath a thin fibrous cap along the lining of a vessel. When subjected to increased rates of hemodynamic pulsating expansion during systole and elastic contraction during diastole associated with excessive exercise, high mechanical stresses may form in the fibrous cap. Such stresses may lead to rupture of the fibrous cap, releasing a shower of potentially life-threatening emboli into the patient's vasculature. It would therefore be desirable to provide apparatus and methods for isolating and treating vulnerable plaques, so as to minimize the risk of sudden rupture.

A number of solutions have been proposed in the prior art for treating weakened vessels and vulnerable plaques, often involving the placement of a stent within the vessel, with or without a drug-eluting coating. Most stents employ a metal alloy framework, which may include a drug-eluting coating. As noted above, the use of metal stents can introduce additional long-term concerns for patients, including the occurrence of endothelial hyperplasia at the ends of the stent, fatigue fracture and stent migration. More recently, drug-eluting coatings have been employed on some stent designs to reduce the incidence of restenosis, although long-term reduction of restenosis using such coatings has yet to be achieved.

In addition, some previously-known stents have sought to employ naturally occurring biodegradable materials, such as fibrin, or synthetic polymers, such as polyglycolic acid. For example, U.S. Pat. No. 5,510,077 to Dinh et al. describes a stent cast from fibrin by charging a solution of fibrinogen and a fibrinogen-coagulating protein, such as thrombin, in liquid form into a mold cavity containing a metal alloy frame, so as to form a fibrin-coated stent when the fibrin cures. That patent discloses that synthetic polymers, and/or drugs, additionally may be mixed and cross-linked with the fibrinogen and thrombin to improve tissue ingrowth and neointimal formation as the fibrin degrades. However, the patent does not alleviate concerns regarding the fate of the metal alloy frame once the fibrin fully degrades. Moreover, it is believed that such coatings may be relatively fragile, and therefore subject to cracking and delamination resulting from bending and torsional stresses applied to the metal alloy frame in situ.

U.S. Pat. No. 5,591,224 to Schwartz et al. and U.S. Pat. No. 6,312,457 to DiMatteo et al. attempt to overcome the shortcomings of the previously-known devices, such as those described in the Dinh patent, using a support structure formed of elastin, polyglycolic acid or other biodegradable polymer instead of a metal alloy frame. DiMatteo also describes that a fibrin layer on the exterior of the device may be used as an adhesive to adhere the device to the vessel wall. Such materials, however, can be relatively difficult to handle and to deliver within the vasculature using conventional delivery systems, and accordingly no commercially practicable products have been realized using such constructions. Likewise, U.S. Pat. No. 7,399,483 to Stimmeder describes compositions suitable for tissue gluing, sealing or hemostasis, in which a composition of solid fibrinogen and solid thrombin is disposed on a biodegradable carrier, such as a collagen sponge. Such products are not intended for intravascular use and continue to require some form of support structure.

A number of previously known systems have been investigated that could enable an adhesive-coated stent or vascular patch to be delivered intravascularly. For example, U.S. Pat. No. 7,044,982 to Millbocker describes methods of repairing internal defects involving an adhesive-coated prosthetic in which the adhesive is encapsulated within a water soluble material so as to be non-adhesive until the prosthetic is placed in contact with tissue. U.S. Pat. No. 7,402,172 to Chin et al. describes an adhesive-coated intraluminal therapeutic patch having a water soluble coating and a slidable sheath disposed on the delivery catheter to prevent premature activation of the adhesive. To date, the systems described in the foregoing patents do not appear to have overcome the problems inherent in intravascularly delivering an adhesive patch without premature or incomplete activation of the adhesive.

IV. SUMMARY OF THE INVENTION

In view of the foregoing, the present invention is directed to methods and apparatus for providing a free-standing biodegradable patch suitable for medical applications, especially intravascular, minimally-invasive and intraoperative surgical applications. In one preferred embodiment, the patch comprises a free-standing film or device comprising a mixture of a solid fibrinogen component and a solid thrombin component that, when exposed to an aqueous environment, undergoes polymerization to form fibrin. The solid fibrinogen and thrombin components may comprise a mixture that forms a continuous layer or may be divided into a plurality of discrete segments. Alternatively, the solid fibrinogen and solid thrombin components may comprise separate layers. In some embodiments, the patch comprise only solid fibrinogen, or solid fibrinogen with a calcium chloride, but without a thrombin component. In accordance with one aspect of the invention, the film or device may take a non-adherent form during delivery to a target location within a vessel or tissue, and thereafter activated to adhere to a vessel wall or tissue.

A patch constructed in accordance with the principles of the present invention may include one or more polymers added to the solid fibrinogen and, if present, thrombin components to improve the mechanical properties of the patch, such as strength and/or flexibility. The patch of the present invention optionally may include one or more additional agents or additives, e.g., Factor XIII, inorganic calcium salts, a plasticizer, radiopaque material, etc. Some embodiments of the patch of the present invention may include one or more therapeutic drugs, genes, or other bioactive agents that elute from the patch into the adjacent tissue or vessel, or are delivered to the surrounding tissue or bloodstream during biodegradation of the patch.

In some embodiments, the patch may be configured for intravascular or minimally-invasive surgical applications to be delivered using an expandable member (e.g., a balloon, cage, or other expandable structure), such that the expandable member may be expanded in situ to place the patch in apposition with tissue or vessel wall. In other embodiments, the patch may be coated or cast directly onto the expandable member. In accordance with another aspect of the invention, a protective layer may be used to temporarily adhere the patch to an expandable member or a protective layer may applied directly to the exterior of the patch.

In accordance with one aspect of the present invention, the patch may be disposed on an expandable member such that only those portions of the patch that contact a tissue or vessel wall by expansion of an expandable member adhere to the tissue or vessel wall, while non-contacting portions remain affixed to the expandable member. In this manner, the patch may be used to provide a protective layer to the inner lumen of a vessel in the vicinity of a vessel bifurcation without occluding a branch vessel.

Methods of making and using a free-standing biodegradable patch in accordance with the present invention are provided.

V. BRIEF DESCRIPTION OF THE DRAWINGS

VI. DETAILED DESCRIPTION OF THE INVENTION

Figure 1:
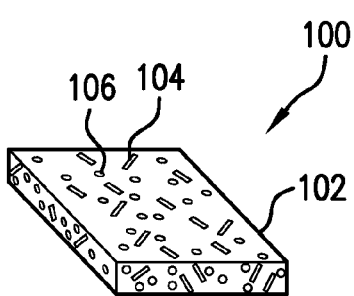
FIG. 1 is a schematic view of a first illustrative embodiment of a patch of the present invention.

The present invention is generally directed to a free-standing biodegradable patch for use in medical procedures for supporting, protecting or joining weakened tissue or vessels, including interventional, minimally-invasive and intraoperative surgical procedures. The patch of the present invention also may be used for isolating, occluding and/or treating deposits of vulnerable plaque, aneurysms and fistulas.

In accordance with one aspect of the invention, the patch may incorporate therapeutic drugs, genes or other bioactive agents that are eluted into the surrounding tissue to provide localized treatment or into an adjacent bloodstream to provide systemic treatment. Alternatively, such drugs, genes or other bioactive agents may be released into surrounding tissue or an adjacent bloodstream as the patch biodegrades. The patch of the present invention also may include one or radiopaque materials to enhance visibility and placement of the patch during deployment. The patches described herein may be delivered to a portion of the body using one or more delivery systems, which are per se known. In some embodiments, the delivery system may comprise one or more expandable members (e.g., an expandable cage, a balloon, and the like), as described herein below.

In accordance with one aspect of the present invention, free-standing biodegradable patches are provided that function beneficially when delivered in the body. For example, the patch may provide mechanical support to tissue, such as where a patch is delivered intraluminally to the interior of a blood vessel to prevent restenosis or narrowing of the blood vessel. In other contexts, the inventive patch may be deployed in a vessel to seal and support a dissection in a vessel wall caused by balloon dilatation. In patients that have suffered an aneurysm, the inventive patch may be used to isolate and/or stabilize a weakened vessel wall.

The patches of the present invention additionally may provide a sealing or holding function. For example, a patch constructed in accordance with the present invention may be used to seal a perforation in a blood vessel or other hollow body organ, such as may arise during a percutaneous procedure. In other instances, a patch may be used to seal a vulnerable plaque, thereby allowing drugs to be delivered to the plaque to stabilize or dissipate the plaque without damaging the thin fibrous cap. In such applications, the patch also may promote endothelialization of the lesion. In still other instances, the patch may be employed to retain two tissue surfaces in apposition, for example, to secure two vessels that are joined during an anastomosis.

In accordance with another aspect of the invention, the patch of the present invention additionally aids in endothelialization (i.e., the process of tissue regrowth over a stent or other foreign body). In particular, the inventive patch will form a fibrin matrix in situ, thus providing a scaffold in and on which tissue may grow. When a patch is used to cover a lesion in the vasculature, such as a vulnerable plaque or a preexisting stent, the endothelialization provided by the adhesive may reduce the risk of plaque rupture, neointimal hyperplasia or restenosis.

Patches constructed in accordance with the present invention also may be used to deliver one or more therapeutic agents to tissue, as mentioned above. For example, in some instances a stent may have been placed into a vessel to provide mechanical support. In these instances, a patch of the present invention may be placed within or around the stent to deliver an anti-restenosis agent, which may reduce the risk of in-stent restenosis and eliminate the need for stent-in-stent implantation. Additionally, the patch of the present invention may promote endothelialization by delivery of growth factors. In still other instances, one or more patches may be used to attach endothelial cells to the inside of the lumen to promote healing. In yet another proposed application, a patch of the present invention may be delivered, e.g., using a bronchoscope balloon, within a patient's bronchus or trachea to deliver chemotherapy or an anti-cancer drug through the patient's vasculature or tissue.

Although foregoing examples are directed toward intraluminal delivery of the inventive patch, it should be noted that patches constructed in accordance with the present invention may be delivered to any suitable portion of the anatomy. For example, one or more adhesives may be delivered to one or more hollow body organs, such as the esophagus, stomach, intestines, bronchus, trachea, urethra, ureters, the sinuses, the ears, or the heart. In embodiments configured for use in a heart, the patch may be used to treat or seal a patent foramen ovale, a paravalvular leak, the left auricular appendage, or the like. In other embodiments, the inventive patches may be used to modify the geometry of the left ventricle, and thus reduce functional mitral regurgitation.

Patch Composition

In a preferred embodiment, the patch of the present invention comprises a mixture of, or separate layers of, a solid fibrinogen component and a solid thrombin component, configured to form a free-standing biodegradable film or article. When exposed to an aqueous environment, e.g., blood, the fibrinogen and thrombin components undergo polymerization in situ to form a solid fibrin film or article. This polymerization models the final stages of the clotting cascade to create a fibrin matrix similar to clots that form naturally in the human body. In accordance with one aspect of the present invention, a suspension of fibrinogen is formed using a non-aqueous solvent, such as ethanol. A predetermined amount of thrombin is dissolved in the non-aqueous solvent, and mixed with the fibrinogen suspension. The mixture then is poured into a mold, and the solvent evaporated, leaving a solid free-standing film or patch comprising unreacted fibrinogen and thrombin components. Because, in accordance with the present invention, the fibrinogen and thrombin are combined in a non-aqueous environment, the components do not polymerize to form fibrin until the patch is exposed to an aqueous environment, such as blood.

It is expected that commercially available fibrinogen products may be used to prepare a patch in accordance with the present invention, although commercial fibrinogen products that include excipients or stabilizers, such as sodium citrate or sodium chloride, have been observed to provide a relatively inflexible and fragile patch. On the other hand, commercially available purified human fibrinogen products prepared without any excipients have been observed to produce patches, when made as described herein below, having greater integrity and flexibility. One commercially available fibrinogen product that has been observed to provide satisfactory results in initial tests is Part No. PP001S, available from Hyphen Biomed, Neuville-sur-Oise, France, distributed in the United States by Aniara Corporation, Mason, Ohio. This "unsalted" fibrinogen product is used in the Examples described below.

It is expected that commercially available thrombin also may be used to prepare a patch in accordance with the present invention. Initial tests conducted with human thrombin, Part No. AEZ0060, available from Hyphen Biomed, Neuville-sur-Oise, France, distributed in the United States by Aniara Corporation, Mason, Ohio, have produced satisfactory results. In addition, the presence of some excipients in commercial sources of thrombin have not been observed to effect the mechanical characteristics of the patch.

Unlike previously-known fibrin coated stents such as those described in the Dinh patent, wherein fibrinogen and thrombin are reacted in vitro to form stent coatings, in the present invention the fibrinogen and thrombin are polymerized only after being delivered to the target location. When combined in a moist environment, thrombin converts fibrinogen into fibrin monomers, which are in turn polymerized to form fibers. These fibrin fibers join together into a network structure, resulting in a fibrin matrix. The patch of the present invention may include one or more additional components, such as calcium, Factor XIII and bovine aprotinin, which may affect the rates of polymerization and biodegradation. Importantly, because fibrin is a part of the body's natural clotting mechanism, the in situ formed fibrin patches of the present invention are biocompatible, non-thrombogenic, biodegradable, and have a high affinity for various biological surfaces.

As a further alternative, a patch in accordance with the present invention may comprise a layer of solid fibrinogen, preferably unsalted, as described above). Such fibrinogen-only or fibrinogen plus calcium salt patches are expected to have different mechanical properties when delivered to tissue compared to patches that contain thrombin. As explained earlier, however, the addition and amount of calcium salt may be tailored to obtain specific mechanical properties for a patch, as may be suitable for particular applications.

The patches of the present invention may be formed as a solid film or patch using any of a number of deposition techniques, and as described below, may include therapeutic agents or radio-opacifiers. The fibrinogen and, if present, thrombin components may be deposited on a surface via spray coating, dip coating, brushing, rolling, spinning, inkjet printing, or the like. In some instances, as will be described in more detail below, a patch may be formed directly onto one or more portions of one of the delivery systems described here, such as one or more balloons. In other instances, a patch may be formed on a temporary protective layer, which may be removed before, during, or immediately prior to delivery of the patch. Preferably, the patch should have sufficient structural integrity so as to be free-standing when removed from the delivery system or temporary protective layer.

As noted above, the physical properties of a patch may change during the polymerization process, after exposure to a moist environment. Generally, as the polymerization process begins (e.g., when thrombin and fibrinogen are combined in the presence of water), the patch may temporarily become a gel and become highly adherent. Generally, it is expected that the patch may be freely manipulated, stretched, or deformed when in its temporary gel form. The duration of the gel stage may be dependent on the relative and overall concentrations of the fibrinogen and thrombin components, as well as the presence of any other components.

Both the relative and overall concentrations of each of the patch components may affect the rate of fibrin polymerization, as well as the physical characteristics of the resulting fibrin matrix. For example, a higher concentration of thrombin in a patch may shorten the setting time, thereby decreasing the amount of time the patch remains in a gel form. A higher thrombin concentration also is expected to produce a supple fibrin matrix with relatively low load-bearing capabilities. Conversely, a higher concentration of fibrinogen may increase the setting time for the patch, result in a less porous and stiffer fibrin matrix, and decrease the degradation rate of the patch. Other patch additives, such as calcium, Factor XIII, aprotinin, or other additives (e.g., plasticizers, radio-opacifiers, film-forming agents and the like) also may affect the resulting fibrin matrix. As such, the composition of the patch may be tailored to achieve a preferred setting time, matrix stiffness, porosity, and degradation rate, depending upon the intended application.

As mentioned above, the patch may include one or more additives that may affect the formation of a fibrin matrix. For example, a patch may include Factor XIII, which when activated, forms cross-links between fibrin molecule chains that stiffen the fibrin matrix. In other variations, a patch may include an inorganic calcium salt such as calcium chloride. Because calcium ions serve as a cofactor in the conversion of fibrinogen to fibrin, the presence of these calcium salts may increase the rate of polymerization. Additionally, because calcium ions are required for the activation of Factor XIII, their presence may affect the extent of cross-linking in the fibrin matrix.

In some embodiments, a patch constructed in accordance with the principles of the present invention may comprise one or more plasticizers that may increase the flexibility of the patch, improving the patch integrity and making it less prone to cracking or flaking. Examples of suitable plasticizers include, but are not limited to, phthalate esters (e.g., diethyl phthalate), sebacate esters (e.g., dibutyl sebacate), citrate esters (e.g., triethyl citrate, tributyl citrate), glycerol derivatives (e.g., propylene glycol, poly(ethylene glycol)), surfactants, preservatives, combinations thereof, and the like. The amount of plasticizer may vary depending on the intended application as well as the desired flexibility for the patch, and generally will comprise less than about 50% of the constituents used to prepare the patch.

In other embodiments, a patch may comprise one or more radio-opacifier substances that allow the patch to be imaged fluoroscopically prior to, during, or after implantation. Examples of suitable radio-opacifiers include, but are not limited to, materials containing bismuth, barium (e.g., barium sulphate), gold, iodine, platinum, or tantalum, zirconium oxide and iron oxide. In some embodiments described below, the radio-opacifier may be provided in high concentrations in only discrete areas of the patch.

The patch of the present invention optionally may incorporate one or more film-forming agents. Generally, a film-forming agent may assist in forming a continuous film during the deposition process, and may include one or more biodegradable polymers, such as, for example, polycarboxylic acid, polyanhydrides (e.g., maleic anhydride polymers), polyorthoesters, poly-amino acids, poly(carbonate), polyethylene oxide, poly(glutarunic acid), polyphosphazenes, poly-lactic acid, polyglycolic acid, poly(L-lactic acid), poly(D,L,-lactide), poly(lactide acid-co-glycolic acid), 50/50 (DL-lactide-co-glycolide), polydioxanone, polypropylene fumarate, polydepsipeptides, polycaprolactone, (D,L,-lactide-co-caprolactone), poly-caprolactone co-butlacrylate, polyhydroxybutyrate valerate, polycarbonates (e.g., tyrosine-derived polycarbonates and arylates), polyiminocarbonates, cyanoacrylate, calcium phosphates, poluglycosaminogycans, polysaccharides (e.g., hyaluronic acid, cellulose, and hydroxypropylmethyl cellulose), gelatin, starches, dextrans, alginates, proteins, polypeptides, surface erodible polymers (e.g., polyhydroxybutyrate, polycaorolactone, polyanhydrides (both crystalline and amorphous), maleic anhydride copolymers, and zinc-calcium phosphate), copolymers thereof, derivatives thereof, mixtures thereof, and the like.

In accordance with another aspect of the present invention, the patch optionally may incorporate one or more therapeutic agents intended for local or systemic delivery. When a patch is delivered into the body, the therapeutic agent may be at least temporarily stored in the patch. In some variations, the therapeutic agent may diffuse out of the patch. In other variations where the patch is biodegradable, the therapeutic agent may be released from the patch as the patch biodegrades. The selection of therapeutic agent or agents, the timing of delivery, and the overall amount of therapeutic agent released from the patch may be determined by the intended treatment plan, and a specific composition for the patch may be chosen to achieve this release profile. In variations where the patch includes one or more additional components (e.g., a plasticizer, a film-forming agent, etc.), any of the additional components may incorporate one or more therapeutic agents.

Examples of suitable therapeutic agents include, but are not limited to anti-inflammatory agents, anti-allergenic agents, anti-bacterial agents, anti-viral agents, anticholinergic agents, antihistamines, antithrombotic agents, anti-scarring agents, antiproliferative agents, antihypertensive agents, anti-restenosis agents, healing promoting agents, vitamins, biological molecules such as proteins, genes, growth factors, cells and DNA, combinations thereof, and the like.

Examples of suitable anti-allergenic agents that may be suitable for use with the described methods and devices include, but are not limited to, pemirolast potassium (ALAMAST®, Santen, Inc.) and any prodrugs, metabolites, analogs, homologues, congeners, derivatives, salts and combinations thereof. Examples of antiproliferative agents include, but are not limited to, actinomycin D, actinomycin IV, actinomycin 11, actinomycin X1, actinomycin $C_1$, and dactinomycin (COSMEGEN®, Merck & Co., Inc.). Examples of healing promoting agents include, but are not limited to, sirolimus, everolimus, temsiolimus, and vitamin A.

Examples of antiproliferative agents that may be suitable for use with the described methods and devices include, but are not limited to, angiopeptin, angiotensin converting enzyme inhibitors such as captopril (CAPOTEN® and CAPOZIDE®, Bristol-Myers Squibb Co.), cilazapril or lisinopril (PRINIVIL® and PRINZIDE®, Merck & Co., Inc.); calcium channel blockers such as nifedipine; colchicines; fibroblast growth factor (FGF) antagonists, fish oil (omega 3-fatty acid); histamine antagonists; lovastatin (MEVACOR®, Merck & Co., Inc.); monoclonal antibodies including, but not limited to, antibodies specific for Platelet-Derived Growth Factor (PDGF) receptors; nitroprusside; phosphodiesterase inhibitors; prostaglandin inhibitors; suramin; serotonin blockers; steroids; thioprotease inhibitors; PDGF antagonists including, but not limited to, triazolopyrimidine; and nitric oxide, and any prodrugs, metabolites, analogs, homologues, congeners, derivatives, salts and combinations thereof.

Examples of anti-bacterial agents that may be suitable for use with the described methods and devices include, but are not limited to, aminoglycosides, amphenicols, ansamycins, β-lactams such as penicillins, lincosamides, macrolides, nitrofurans, quinolones, sulfonamides, sulfones, tetracyclines, vancomycin, and any derivatives or combinations thereof. Examples of penicillins that may be suitable for use with the described methods and devices include, but are not limited to, amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin G benethamine, penicillin G benzathine, penicillin G benzhydrylamine, penicillin G calcium, penicillin G hydrabamine, penicillin G potassium, penicillin G procaine, penicillin N, penicillin 0, penicillin V, penicillin V benzathine, penicillin V hydrabamine, penimepicycline, phenethicillin potassium, piperacillin, pivampicillin, propicillin, quinacillin, sulbenicillin, sultamicillin, talampicillin, temocillin, and ticarcillin.

Examples of anti-viral agents suitable for use with the described methods and devices include, but are not limited to, acyclovir, famciclovir, valacyclovir, edoxudine, ganciclovir, foscarnet, cidovir (vistide), vitrasert, formivirsen, HPMPA (9-(3-hydroxy-2phosphonomethoxypropyl)adenine), PMEA (9-(2-phosphonomethoxyethyl)adenine), HPMPG (9(3-Hydroxy-2-(Phosphonomet-hoxy)propyl)guanine), PMEG (9-[2-(phosphonomethoxy)ethyl]guanine), HPMPC (1-(2-phosphonomethoxy-3-hydroxypropyl)cytosine), ribavirin, EICAR (5-ethynyl-1-beta-D-ribofuranosylimidazole-4-carboxamine), pyrazofurin(3-[beta-D-ribofuranosyl]-4-hydroxypyrazole-5-carboxamine), 3-Deazaguanine, GR92938X (1-beta-D-ribofuranosylpyrazole-3,4-dicarboxami-de), LY253963 (1,3,4-thiadiazol-2-ylcyanamide), RD3-0028 (1,4-dihydro-2,3-Benzodithiin), CL387626 (4,4'-bis[4,6-d][3-aminophenylN—,N-bis(2-carbamoylethyl)-sulfonilimino]-1,3,5-triazin-2-ylamino-biphenyl-2-,2'-disulfonic acid disodium salt), BABIM (Bis[5-Amidino-2-benzimidazoly-I]-methane), NIH351, and combinations thereof.

Anti-inflammatory agents may include steroidal and nonsteroidal anti-inflammatory agents. Examples of suitable steroidal anti-inflammatory agents include, but are not limited to, 21 acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, any of their derivatives, and combinations thereof.

Examples of suitable nonsteroidal anti-inflammatory agents include, but are not limited to, COX inhibitors. These COX inhibitors may include COX-1 or COX nonspecific inhibitors such as, for example, salicylic acid derivatives, aspirin, sodium salicylate, choline magnesium trisalicylate, salsalate, diflunisal, sulfasalazine and olsalazine; para-aminophenol derivatives such as acetaminophen; indole and indene acetic acids such as indomethacin and sulindac; heteroaryl acetic acids such as tolmetin, dicofenac and ketorolac; arylpropionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam) and alkanones such as nabumetone. The COX inhibitors may also include selective COX-2 inhibitors such as, for example, diaryl-substituted furanones such as rofecoxib; diaryl-substituted pyrazoles such as celecoxib; indole acetic acids such as etodolac and sulfonanilides such as nimesulide).

Examples of suitable biomolecules include, but are not limited to, peptides, polypeptides and proteins; oligonucleotides; nucleic acids such as double or single standard DNA (including naked and eDNA), RNA, antisense nucleic acids such as antisense DNA and RNA, small interfering RNA (siRNA), and ribozymes, genes, carbohydrates. Nucleic acids may be incorporated into one or more vectors (including viral vectors), plasmids, liposomes, or the like.

Examples of suitable proteins include, but are not limited to serca-2 protein, monocyte chemoattractant proteins ("MCP-1") and bone morphogenic proteins ("BMPs"), such as, for example. BMP-2 (OP-1), BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15. These BMPs may be provided as homodimers, heterodimers, or combinations thereof. In some variations, molecules capable of inducing an upstream or downstream effect of a BMP may be provided. This may include, for example, one or more "hedgehog" proteins, or the DNA encoding them. Examples of suitable genes include, but are not limited to survival genes that protect against cell death (e.g., anti-apoptotic Bcl-2 family factors and Akt kinase); SERCA 2 gene; and combinations thereof. In some variations, one or more therapeutic agents may comprise one or more angiogenic factors, such as acidic and basic fibroblast growth factors, vascular endothelial growth factor, epidermal growth factor, vascular endothelial growth factor, epidermal growth factor, transforming growth factor and, platelet-derived endothelial growth factor, platelet-derived growth factor, tumor necrosis factor, hepatocyte growth factor, and insulin like growth factor. In some variations, a therapeutic agent may comprise one or more cell cycle inhibitors (e.g., a cathepsin D (CD) inhibitor). Examples of suitable anti-restenosis agents include, but are not limited to, Rb, nFkB and E2F decoys, thymidine kinase ("TK"), combinations thereof, and the like.

Examples of suitable small molecules include, but are not limited to, hormones, nucleotides, amino acids, sugars, and lipids and compounds have a molecular weight of less than 100 kD. Examples of suitable cells include, but are not limited to, stem cells, progenitor cells, endothelial cells, adult cardiomyocytes, smooth muscle cells, side population (SP) cells, lineage negative (Lin-) cells (e.g., Lin-CD 34−, Lin-CD34+, Lin-cKit+, and the like), mesenchymal stem cells including mesenchymal stem cells with 5-aza, cord blood cells, cardiac or other tissue derived stem cells, whole bone marrow, bone marrow mononuclear cells, whole bone marrow, bone marrow mononuclear cells, endothelial progenitor cells, skeletal myoblasts or satellite cells, muscle derived cells, go cells, endothelial cells, adult cardiomyocytes, fibroblasts, smooth muscle cells, adult cardiac fibro blasts +5-aza, genetically modified cells, tissue engineered grafts, MyoD scar fibroblasts, pacing cells, embryonic stem cell clones, embryonic stem cells, fatal or neonatal cells, immunologically masked cells and teratoma derived cells. Cells may be of human origin (autologous or allogenic), of animal origin (xenogenic), or may be genetically engineered. Any of the foregoing drugs or biologically active molecules may be encapsulated, for example, in microparticles or liposomes, prior to incorporation within the patch.

Other bioactive agents useful in the present invention include, but are not limited to, free radical scavengers; nitric oxide donors; rapamycin; methyl rapamycin; everolimus; tacrolimus; 40-O-(3-hydroxy)propyl-rapamycin; 40-O-[2-(2-hydroxy)ethoxy]ethyl-rapamycin; tetrazole containing rapamycin analogs; estradiol; clobetasol; idoxifen; tazarotene; alpha-interferon; host cells including, but not limited to prokaryotes and eukaryotes such as, for example, epithelial cells and genetically engineered epithelial cells; dexamethasone; and, any prodrugs, metabolites, analogs, homologues, congeners, derivatives, salts and combinations thereof.

Patch Configurations

Patches constructed in accordance with the principles of the present invention may be manufactured in either an adherent or non-adherent state. Alternatively, a patch may be manufactured in a non-adherent state, and activated prior to use, for example, by dipping in warm water prior to application or delivery to the body. As yet another alternative, the patch may include a water-soluble protective coating, for example, for intravascular applications, to prevent the fibrin polymerization process from beginning before the patch is delivered to a target location.

Referring now to FIG. 1, a first embodiment of a patch constructed in accordance with the principles of the present invention is described. Patch 100 comprises free-standing single layer 102 formed from a mixture of unreacted fibrinogen 104 and thrombin 106, prepared as discussed above. Patch 100 may include one or more additional components or agents, such as those described above. As a further alternative, thrombin 106 may be omitted entirely. Preferably, patch 100 has a thickness in a range of 50 µm-200 µm, and more preferably 30 µm-500 µm, sufficient to provide a free-standing article. Alternatively, layer 102 may be built-up by deposition of several thinner films. In one preferred embodiment, the ratio of thrombin is about 0 to 1 NIH per mg of fibrinogen and the ratio of inorganic calcium salt (e.g., $CaCl_2$) is 0 to 5 mg per mg of fibrinogen. In addition, patch 100 preferably includes a plasticizer, such as polyethylene glycol, in a ratio from 0 to 0.5 mg per mg of fibrinogen. A therapeutic agent, if present, may be multiples of the patch weight, for example, about 0 to 10 mg therapeutic agent per mg of fibrinogen. For slow release therapeutic applications, however, applicant expects a ratio of about 0 to 1 mg therapeutic agent per mg of fibrinogen to be more suitable.

Figure 2:
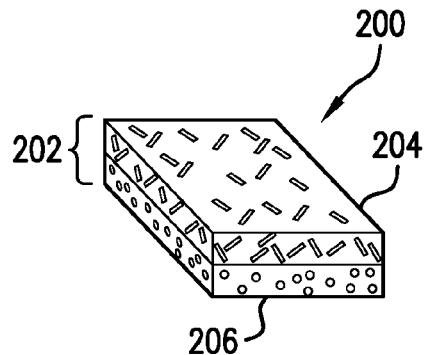
FIG. 2 is a schematic view of an alternative illustrative embodiment of a patch of the present invention wherein the constituents are arranged in separate layers.

FIG. 2 illustrates an alternative embodiment the present invention, in which patch 200 comprises separate sublayers of unreacted fibrinogen component and thrombin component. In particular, patch 200 comprises fibrinogen sub-layer 204 and thrombin sub-layer 206. In some alternative embodiments, sub-layer 206 may be omitted entirely, the thrombin to polymerize the fibrinogen may be supplied by the environment in situ. In other embodiments, fibrinogen sub-layer 204 and thrombin sub-layer 206 may be separated by a water-soluble protective layer. In some variations, the protective layer may at least temporarily protect the sublayers from certain substances or stimuli prior to or during delivery, for example, exposure to moisture, to prevent premature activation. Alternatively, the protective layer may be selectively removed to control the activation of the patch. In embodiments in which the patch is already in an adherent form, a protective layer may help prevent premature adhesion between the patch and surrounding tissue. In other instances, the protective layer may protect the patch from mechanical damage prior to or during delivery. In still other embodiments, a protective layer may allow a patch to be folded without adhering to itself. In yet other embodiments, a protective layer may be used to at least temporarily join a patch to a delivery system, as described below.

In some embodiments, a protective layer may be removed from the patch prior to or during delivery of the patch. In this way, a patch may be configured such that only the fibrin-forming layers (as well as an additives or therapeutic agents) are delivered to tissue. The protective layer may be made from a water-soluble material, a material that is soluble in another media, a material that is electrolytically decomposable, a bioerodable or biodegradable material, combinations thereof, or the like. Examples of suitable water-soluble materials include, but are not limited to, polysaccharides (e.g., hyaluronic acid, cellulose, hydroxypropylmethyl cellulose, gelatin, starches, dextrans, alginates, their derivatives, and the like), contrast agents (e.g., diatrizoate, metrizoate, ioxaglate, iopamidol, iohexol, ioxilan, iopromide, iodixanol, and the like), sugar-based polymers (e.g., sucrose), water-soluble hydrogels, combinations thereof, and the like.

Figure 3:
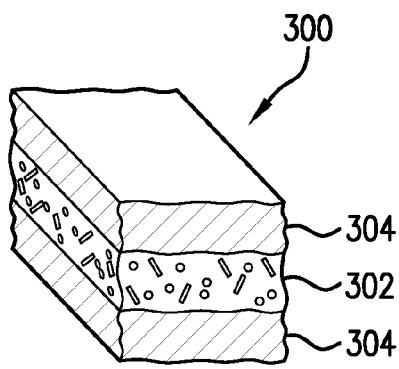
FIG. 3 is a schematic view of another alternative illustrative embodiment of a patch of the present invention in which a mixture of solid fibrinogen and solid thrombin components is sandwiched between protective layers.

In FIG. 3, patch 300 is described that includes fibrin-forming layer 302 and protective layers 304. While patch 300 is depicted in FIG. 3 as having protective layer 304 on both sides of layer 302, the patch may include only one protective layer 304 attached thereto. In still other embodiments, patch 300 may comprise a single layer 302 of a mixture of unreacted fibrinogen and thrombin, which protective layer 304 covers all of the exposed surfaces of the patch. While shown in FIG. 3 as having single layer 302 of unreacted fibrinogen and thrombin (similar to that described with respect to FIG. 1), patch 300 may comprise any number of fibrin-forming layers 302, each of which may include different formulations, e.g., different ratios of thrombin to fibrinogen, or different amounts of plasticizer, as required for a particular application. Such construction may provide layers having different setting or degradation times, different stiffness, or release different drugs. As such, multiple adhesive layers may provide a user with additional flexibility in creating a patch in accordance with the present invention.

Figure 4:
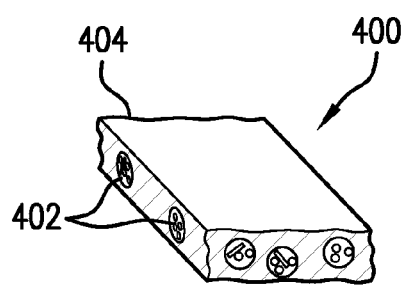
FIG. 4 is a schematic view of another alternative illustrative embodiment of a patch of the present invention wherein discrete segments of the mixture of solid fibrinogen and solid thrombin components are embedded in a water soluble protective layer.

Referring to FIG. 4, a further alternative of a patch constructed in accordance with the principles of the invention is described. Patch 400 comprises discrete or interconnected portions or strands 402 of solid unreacted fibrinogen and thrombin disposed within matrix 404. Matrix 404 may be a water-soluble material, such as those described above, or may be made from a biodegradable or bioerodible material, such as the biodegradable polymers described above. In some of these variations, matrix 404 may protect the fibrin-forming components 402 from premature activation. Additionally, matrix 404 may provide patch 400 with additional flexibility or rigidity, as may be desired for a particular application.

When patch 400 is delivered, e.g., through the vasculature of a patient, the solid unreacted fibrinogen and thrombin portions 402 may adhere to tissue. However, matrix 404, which may be a water-soluble material, initially protects the fibrin-forming components from polymerizing. As water-soluble matrix 404 dissolves during exposure within the body, portions 402 are exposed, thereby initiating polymerization. Such exposure also may allow the fibrin gel to adhere to the bodily tissue and cure to form a fibrin-matrix patch. Pressure applied by a delivery device (e.g., by an inflated balloon), may cause portions 402 to join and form a continuous film within the body. In other embodiments, matrix 404 may be a biodegradable material, such that exposed portions of the unreacted fibrin-forming components 402 become adherent, thereby allowing patch 400, including biodegradable matrix 404, to adhere to surrounding tissue.

Figure 5A:
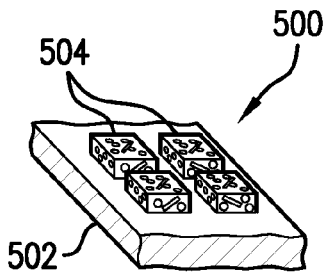
FIGS. 5A-5D are, respectively, a schematic view of a further alternative embodiment of the patch of present invention wherein discrete segments of the mixture of solid fibrinogen and solid thrombin components are arranged on a protective layer, and illustrative views showing application of the patch of FIG. 5A to a target location.

In other variations, a patch of the present invention may be formed with the unreacted fibrinogen and thrombin components, or just a fibrinogen component, arranged in predetermined patterns. For example, in some variations, the fibrin-forming components may be arranged in a mesh-like pattern. In still other variations, the fibrin-forming components may be divided into a plurality of discrete segments. FIGS. 5A-5D illustrate one such variation, patch 500. FIG. 5A is a perspective view of patch 500, which includes protective layer 502 and fibrin-forming segments 504 deposited on protective layer 502. While shown in FIG. 5A as having protective layer 502, it should be appreciated that fibrin-forming segments 504 alternatively may be deposited directly onto one or more portions of a delivery device, with or without a protective layer. An additional protective layer (not shown) may be used to cover some or all of the fibrin-forming segments during delivery.

Figure 5B:
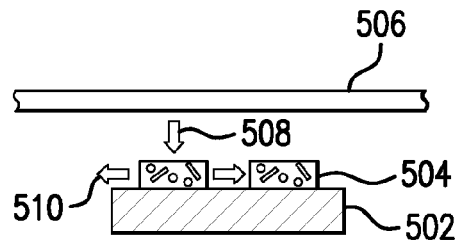
Figure 5C:
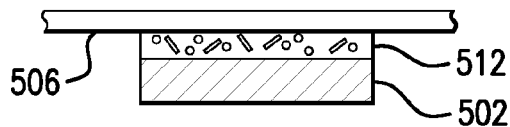
Figure 5D:
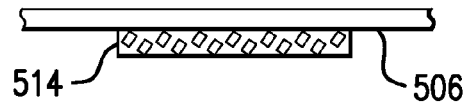

As illustrated in FIGS. 5B through 5D, although fibrin-forming segments 504 may be divided into a number of discrete segments, some or all of the segments 504 may be joined in situ to form a continuous film. More specifically, in embodiments in which segments 504 take on a gel form after activation, the segments may be manipulated or remodeled by the application of one or more forces. For example, when patch 500 described above is pressed against vessel wall 506 by an expandable delivery device (not shown), the device and vessel wall may apply pressure (indicated by the arrows in FIG. 5B) to segments 504 that cause the gelatinous, partially-cured fibrin-forming segments 504 to deform outwardly, as shown by arrows 510. This deformation may in turn cause individual segments 504 to join into solid fibrin film 512, as depicted in FIG. 5C. Protective layer 502 may thereafter be removed or dissolve, such that fibrin-forming segments 504 completer the process of polymerizing to form fibrin matrix 514, as shown in FIG. 5D.

Dividing the unreacted fibrinogen and thrombin components into discrete segments 504 may provide a number of advantages. For example, a patch made up of discrete segments 504 may have additional flexibility compared to a solid continuous layer, thereby enabling the patch to be folded to facilitate transluminal delivery. In other instances, discrete segments 504 may be used to form a continuous patch that will not block a side branch when deployed in a branched blood vessel. In such cases, it is expected that only those segments 504 that contact a tissue surface will deform, and thus segments 504 that do not contact tissue will not contribute to forming a continuous film. As such, if a balloon carrying discrete segments 504 is expanded inside of a branched vessel, those segments that are expanded toward the side branch will not contact tissue, and thus will not become part of the resulting patch.

Figure 6A:
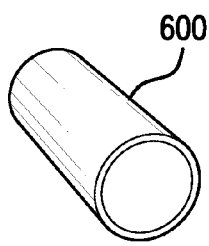
FIGS. 6A-6E are illustrative configurations for articles formed from a mixture of solid fibrinogen and solid thrombin components, or solid fibrinogen, prepared in accordance with the present invention.
Figure 6B:
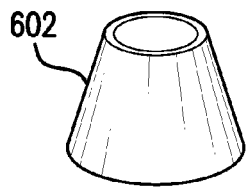

A patch of the present invention may have any suitable size and shape, such that the dimensions of the patch may be determined at least in part by the dimensions of the anatomy in which the patch will be applied. In addition, solid patches of unreacted fibrinogen or thrombin, with or without additional additives as described above, may be modeled into any suitable size of shape, depending upon the intended application. FIGS. 6A-6E illustrate a number of patches and articles modeled from such patches. For example, FIG. 6A illustrates patch 600 having the form of a hollow cylinder, and may find particular utility where the patch will be placed in a cylindrical hollow body organ. Patch 602 of FIG. B illustrates that a patch of the present invention may take on any other three-dimensional shape, such as a frustroconical section.

Figure 6C:
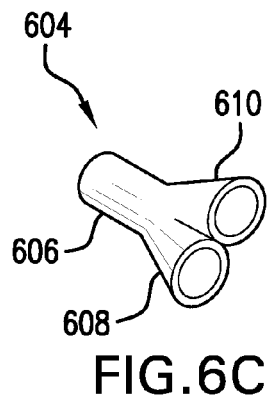

Other suitable three dimensional shapes may include, but are not limited to, spheres, hemispheres and cones. In FIG. 6C, patch 604 is configured as a branched cylinder having main trunk 606 and first 608 and second 610 side branches, such as may be required to provide internal or external support for a branched vessel. While shown in FIG. 6C as having a generally y-shaped configuration, patch 604 may be configured such that side branches 608 and 610 project from main trunk 606 at any desired point along the length of main trunk 606.

Figure 6D:
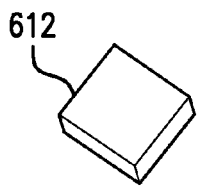
Figure 6E:
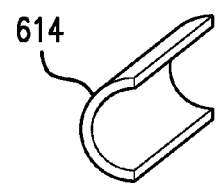

In other embodiments, a patch constructed in accordance with the principles of the present invention may be formed in a flat shape, such as patch 612 of FIG. 6D. While shown in FIG. 6D as being approximately rectangular in shape, patch 612 may be any suitable shape, including, but not limited to, a circle, an oval, a triangle, a square, another polygon, or a shape with irregular geometry. Additionally, patch 612 may be rolled, folded, bent or otherwise modified to form a three-dimensional shape. For example, FIG. 6E shows rectangular patch 614 that has been curved to form a half-cylinder, e.g., to mate with an interior surface of a vessel to occlude or isolate an aneurysm. In other variations, the shape of the patch may be dependent on the system that will deliver it. For example, a patch according to the present invention may be formed by depositing a film of unreacted fibrinogen and thrombin, or just unreacted fibrinogen, without or without a salt component, on a portion of the delivery system (e.g., a balloon). In such instances, the shape of the patch will be the same or similar to the shape of delivery system.

It should be appreciated that the shape and dimensions of a patch may change before or during delivery of the patch. For example, the patch may be folded, crimped, stretched or otherwise deformed in a manner that modifies, temporarily or permanently, the shape of the patch. Furthermore, the ultimate size and shape of the in situ patch formed within the body may differ from the shape of the patch as manufactured. Due to the deformability of the fibrinogen and thrombin components during polymerization, some patches may be molded or otherwise deformed during delivery. For example, in variations where a cylindrical patch is delivered using a balloon, inflation of the balloon may cause the patch to expand to a larger radius.

Delivery Systems and Methods

The patches described herein may be delivered using of a number of previously-known delivery systems, which may comprise one or more expandable members, such as a balloon or expanding mandrel or cage. In embodiments that include an expandable member, the expandable member may be expanded at the delivery site to position a patch so that it is in apposition with tissue. In instances where a patch is placed in a dry environment, or when the delivery system is used to deliver a liquid component, the delivery system may additionally include one or more lines, lumens, ports or the like for delivering water or a liquid component to activate the patch.

In instances where the patch is delivered using a balloon catheter, the balloon may be compliant, semi-compliant, or non-compliant. Non-compliant balloons are relatively inelastic, and the balloon material does not stretch significantly when the balloon is inflated. As such, a deflated non-compliant balloon usually will have excess material that is folded or rolled to place the balloon in a low-profile configuration. Conversely, compliant balloons are relatively elastic, and thus the material tends to stretch and expand when the balloon is inflated. A deflated non-compliant balloon may not have an excess of balloon material, and thus may not need to be folded or rolled. Semi-compliant balloons tend to have an intermediate level of elasticity and upon inflation stretch and expand to a lesser degree than compliant balloons would under similar circumstances. Semi-compliant balloons may or may not need to be rolled or folded.

Figure 7A:
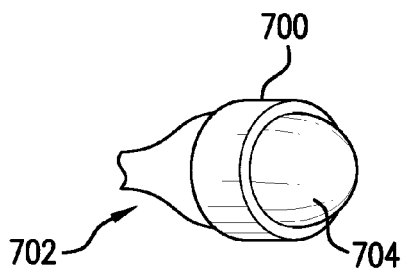
FIGS. 7A and 7B illustrate one method by which a patch of the present invention may be affixed to a balloon catheter.
Figure 7B:
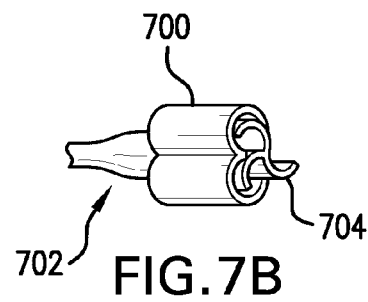

When a balloon catheter is used to deliver a patch of the present invention, the patch may first be placed on or otherwise attached to the balloon. In some variations, a patch may be mechanically attached to the balloon. Alternatively, one or more clips, sutures, coatings or other mechanical structures may be used to hold the patch to the balloon. In variations where a non- or semi-compliant balloon is either folded or rolled, the folding or rolling of the balloon may hold the patch against or to the balloon. FIGS. 7A and 7B illustrate one manner by which a patch may be folded with a non-compliant or semi-compliant balloon to mechanically hold the patch on the balloon. In particular, FIG. 7A depicts cylindrical patch 700 and balloon catheter 702 comprising balloon 704. As shown in FIG. 7A, balloon 704 has been placed inside of the patch 700 and inflated. To hold patch 700, balloon 704 may be deflated and folded. During this process, patch 700 becomes folded along with the non-compliant balloon, as shown in FIG. 7B, such that the resulting folds of balloon 704 temporarily hold patch 700 on the balloon. Patch 700 is released when balloon 704 is later re-inflated.

In other embodiments, the patch may be temporarily attached to the balloon using one or more adhesives, which may be water-soluble and release the patch when exposed to water. For example, in some variations a water-soluble protective layer may be used to join a patch to a delivery system and later release the patch from the delivery system. In other variations, the adhesive may lose its grip on the balloon in response to one or more stimuli (e.g., heat, energy, electricity) which may be applied to the balloon catheter to release the patch in situ.

In still other embodiments, the unreacted fibrinogen and/or thrombin components of the patch may be deposited directly onto the balloon of a delivery catheter using any suitable deposition process. Examples of suitable deposition methods include, but are not limited to, spray coating, dip coating, brushing, rolling, spinning, inkjet printing, casting or the like. Where the patch comprises multiple layers (e.g., protective layers and adhesive layers), each layer may be applied sequentially, and may be applied using the same or different deposition methods. For example, a balloon may first be coated with a protective layer, a layer of unreacted fibrinogen and thrombin then applied, and finally the assembly may be coated with an additional protective layer, such as a water-soluble layer. When multiple discrete segments are used to create the patch, such as described with respect to patch 500 of FIG. 5A, segments 504 may be applied simultaneously or sequentially. Additionally, the final layer of protective coating also may serve to secure the patch to the balloon.

When the fibrin-forming components are used to at least partially coat a balloon, the balloon may be either deflated or inflated when coated. For example, in some variations an inflated non-compliant or semicompliant balloon may be coated with a patch, deflated, and then rolled or folded with the solid patch attached thereto. In other instances, a deflated non-compliant or semicompliant balloon may be rolled or folded, and then coated with a patch. Compliant balloons may be coated when they are at least partially deflated. Additionally, the balloon of a balloon catheter may be made from or coated with a non-stick material, such as PTFE. In this case, the non-stick material may help to prevent the patch from adhering to the balloon during patch activation and delivery. The balloon of the delivery catheter optionally may be textured, dimpled, or otherwise patterned to allow for temporary mechanical adherence between the balloon and the patch.

Figure 8A:
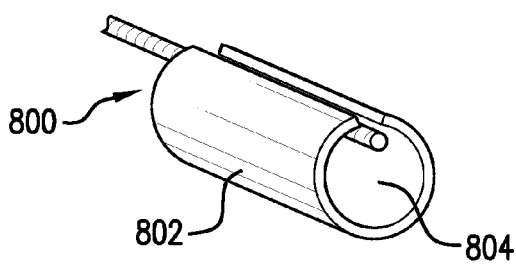
FIGS. 8A and 8B illustrate an alternative balloon catheter that may be used to deliver the patch of the present invention.
Figure 8B:
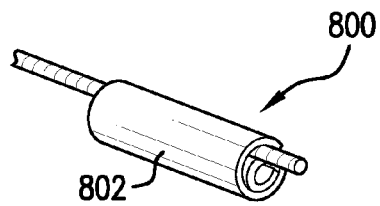

Referring now to FIGS. 8A and 8B, an alternative delivery system suitable for delivering a patch of the present invention is described. Balloon catheter 800 includes curved, rectangular balloon 802 that approximates a cylindrical shape when inflated. When deflated, balloon 802 may be folded or rolled into a spiral, as shown in a FIG. 8B. Because balloon 802 may be laid flat when deflated, balloon catheter 800 may find particular utility in instances where a patch (not shown) is deposited directly on balloon 802, for example, by casting, spraying or using an inkjet printing method. Additionally, because balloon 802 approximates a cylindrical shape when inflated, blood may still pass through lumen 804 defined by balloon 802 during deployment, thereby reducing the risk of upstream ischemia during placement of the patch.

Delivery systems suitable for delivering the patch of the present invention may additionally comprise one or more protective sheaths. Generally, an expandable member may be placed in a low-profile configuration inside of a sheath, and advanced to a target site. At the target site, the sheath may be withdrawn (or the expandable member advanced) to reveal the expandable member. In this way, the sheath may help to shield the patch from exposure to moisture or other stimuli as the patch is advanced through the body. One such delivery system is depicted in FIGS. 9A-9E. Alternatively, the sheath may have a diameter that varies along the length of the catheter, e.g., having a smaller diameter on the shaft and an enlarged diameter in the vicinity of the balloon, so that the sheath does not reduce flexibility of the delivery system.

Figure 9A:
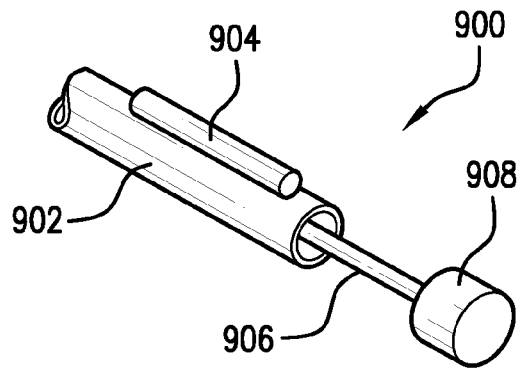
FIGS. 9A-9E illustrate a method of deploying the patch of the present invention in a vessel.
Figure 9B:
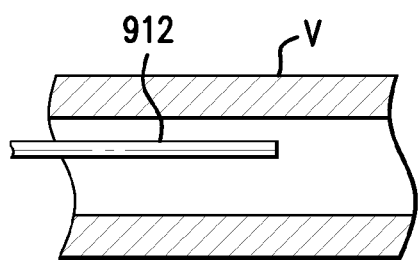
Figure 9C:
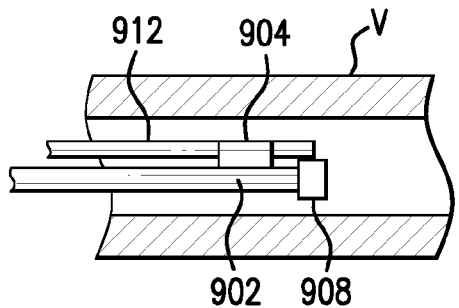
Figure 9D:
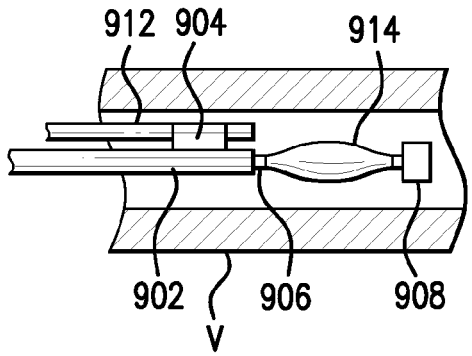
Figure 9E:
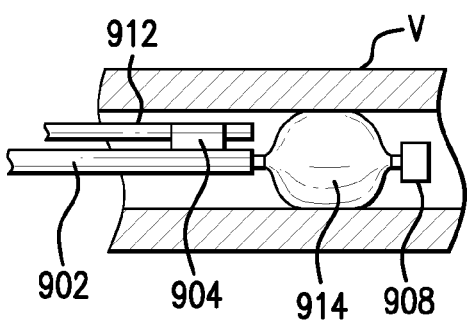

In FIGS. 9A to 9E, delivery system 900 comprises sheath 902, collar 904 disposed on sheath 902, and shaft 906 with cap 908. Cap 908 may be configured to engage the distal end of sheath 902 to seal the interior of sheath 902 from the external environment during advancement of the delivery system through a patient's vasculature. Shaft 906 may be slidable relative to sheath 902 to move cap 908. To deliver a patch within vessel V, guidewire 912 is first advanced to a target site, as shown in FIG. 9B. Sheath 902 then is advanced along guidewire 912 via collar 904, as depicted in FIG. 9C. While shown in FIGS. 9A-9E as having a collar, delivery system 900 need not include such structure, but instead may employ any other structure used for advancing a catheter. Once sheath 902 has been advanced to the target site, shaft 906 is advanced relative to sheath 902 to expose balloon 914 (or another expandable member), as shown in FIG. 9D. Balloon 914 then is expanded to bring the patch (not shown) into apposition with the interior of vessel V. Balloon 914 may be retained in position for a sufficient period of time for the patch to activate and adhere to the vessel wall, e.g., 30 seconds to several minutes. Balloon 914 then is deflated and delivery system 900 removed.

In accordance with another aspect of the present invention, methods are provided for delivering one or more fibrin-matrix forming patches to a body. The patches may be delivered to any suitable portion of the anatomy, including the interior of a blood vessel, and may provide localized or systemic delivery of one or more biological molecules or therapeutic agents. In some applications, the patches may be used to seal a puncture, tear, or dissection in a blood vessel. In other applications, the patches may be used to support a vessel, such as a vessel weakened by aneurysm, or to occlude or isolate an aneurysm or fistula. In still other applications, one or more patches may be used to support or reline a stent disposed within a blood vessel, or to support or seal a vulnerable plaque. The patches of the present invention also may be delivered to the heart, for example, to close a patent foramen ovale, a paravalvular leak, the left auricular appendage, or to modify the geometry of the left ventricle.

As described above, the patch of the present invention may be delivered using any suitable delivery system, such as those described above. The delivery system may comprise a sheath, which may or may not be steerable. Advancement of the delivery system and deployment of the patch may occur under direct visualization, indirect visualization, or a combination thereof. In variations where the delivery system is advanced using indirect visualization, any suitable visualization technique may be used (i.e., fluoroscopy, ultrasound), and either the delivery system or the adhesive may include one or more radiographic components to help aid in visualization.

Once the patch has been advanced to the target location, it may be positioned such that it is in contact with bodily tissues. The delivery system preferably places the patch in contact with bodily tissue such as by expanding an expandable member (e.g. a balloon). In some instances, the expansion of a balloon or other expandable member causes the patch to stretch or deform when in a gel state. The delivery system may continue to hold the patch in contact with the bodily tissue in a stretched or deformed state until the fibrin matrix cures, so as to not diminish the strength of the patch during curing.

The patch may be manufactured in a non-adherent form, and activated at any time prior to or during delivery. Generally, this occurs when the patch is exposed to a moist environment. In some applications, a user may activate a patch prior to introducing the patch into the body. Assuming the setting time for the patch is known, a user may monitor the time remaining before the in situ patch sets. Such embodiments may additionally benefit from a patch composition having a longer setting time (e.g., greater than five minutes), thereby enabling the patch to be advanced to and placed at a target location.

As discussed above, activation of the unreacted fibrinogen and thrombin components may be controlled by the presence of one or more protective layers. In these embodiments, one or more protective layers may protect the patch from activating substances or stimuli. Once the protective layers are removed or dissolve, the fibrin-forming components begin polymerizing. For example, in variations where the patch is covered by a water-soluble protective layer or is impregnated in a water-soluble matrix, the layer or matrix may be configured to dissolve over a predefined period of time when introduced into an aqueous environment. In this way, fibrin polymerization will begin a predetermined interval after introduction into an aqueous environment. In other applications, a user may initiate polymerization by selective removal of a protective layer or applying an activating substance to the patch.

In yet other methods, as described above, the delivery system may control adhesive activation. For example, the patch may be delivered via one or more sealed sheaths, such that activation may be selectively initiated by unsealing the sheath and allowing the patch to be exposed to one or more activating substances or stimuli in the surrounding environment. In other embodiments, the delivery system may be configured to introduce a liquid component to activate the patch prior to deployment, e.g., by flushing a fluid through the interior of the sealed sheath to activate the patch prior to deploying the patch from the sheath.

In embodiments where a delivery system is used to introduce the inventive patch to a target location, the delivery system may be removed at any suitable time. In some applications, the delivery system may be removed once the patch has been placed in contact with bodily tissue, but before it has fully set. In other applications, the delivery system may be retained in position until the patch has fully set. Placement of patch may be confirmed via direct or indirect visualization prior to removal of the delivery device.

EXAMPLES

A patch in accordance with the principles of the present invention was prepared using commercially available fibrinogen, thrombin and calcium chloride. It was observed that the type, amount and ratio of these components significantly affects the properties of the patch, including flexibility, microstructure, and adhesive strength. As discussed in later examples, it was found that the addition of additives rendered the patch more flexible.

Example 1

Fibrinogen powder was prepared by grinding 25 mg of commercially available fibrinogen and suspending it in 1 ml of ethanol. 10 NIH of commercially available thrombin was first dissolved in 2 ml of water. 4.4 mg of $CaCl_2$ was dissolved in 1 ml of ethanol. 160 µl of thrombin solution was added to the $CaCl_2$ solution and mixed. The resulting mixture was added to the fibrinogen suspension, mixed, and then poured into a circular mold having a surface area of 10 $cm^2$. The mold was placed under 30 mm Hg vacuum for three hours to evaporate the ethanol and water. A free-standing patch was formed having sufficient strength to be removed from the mold. The patch, when exposed to saline, became elastic and adhesive.

The strength of the patch in its dry state is important, as the patch must have sufficient structural integrity to be freestanding, and yet retain sufficient flexibility to be configured for delivery via a delivery system, e.g., wrapped around a balloon and tightly folded. Several parameters were observed to effect the strength and flexibility of the patch, including:

The components: Fibrinogen may be prepared in different forms and by various methods. It was observed from experimenting with different sources of fibrinogen that an un-salted preparation of fibrinogen may produce the most desirable results. The presence of salts (usually added during lyophilization of fibrinogen and for stability purposes) can render the resulting patch very brittle. Likewise, it was observed that preparations of pure thrombin provided greater flexibility of the patch.

Additives: Various types of plasticizers were investigated as potential additives, including PEG-6000, PEG-3000, PEG-1500, PEG-400, glycerol, and polyvinyl pyrrolidone (PVP) in different percentages. It was observed that 5-30 wt % of PEG-400 added to the patch preparation produced desirable results.

Storage conditions: It was observed that after the patches were dried in vacuum and the ethanol removed, storing the patches in humid environment significantly improved the flexibility of the patches. Preliminary testing showed a relative humidity of 40-60% provided acceptable results. Such storage conditions were maintained for patches later wrapped around the balloons of delivery systems, as described in later Examples.

Example 2

25 mg of unsalted fibrinogen was suspended in 1 ml ethanol and 100 µl of a 100 mg/mi solution of PEG-400 was added to the fibrinogen suspension. A thrombin solution containing $CaCl_2$ was prepared as in Example 1 and mixed with the suspension of fibrinogen and PEG-400. The resulting mixture was mixed and poured into a circular mold having a surface area of 10 $cm^2$ and then placed under 30 mm Hg vacuum for three hours to dry. The patch was measured to have a thickness of about 150 µm, and was stored in an environment with 60% humidity.

Example 3

A delivery system suitable for delivering a patch as described in the preceding examples was prepared including a standard angioplasty catheter onto which a water soluble coating was applied to ensure release of the patch from the balloon. A water soluble coating of either PEG-6000 or Polyvinylpyrrolidone (PVP) dissolved in ethanol has been determined to be particularly useful. When initially sprayed onto a balloon, solutions of PEG-6000 and PVP become adherent in high concentrations, however, the stickiness disappears as the solution dries into a film. The water soluble coating has been observed to serve two roles: (i) it acts as a temporary glue to adhere the patch to the delivery system; and (ii) during delivery and when immersed in saline or body liquids, the coating dissolves and releases the patch from the delivery system.

A patch made in accordance with the present invention can be wrapped around the balloon of a balloon catheter in several ways. In a first method, the balloon is totally inflated, sprayed first with a water soluble coating, and then the patch wrapped around the balloon while the water soluble coating is still wet; the balloon then is deflated, dried, and folded. In a second method, the balloon is totally deflated, and may be held under negative pressure (such as applied by a syringe). In this second method, the balloon is sprayed with a water soluble coating, the patch is wrapped around the balloon, and the assembly then is dried and folded. In yet a third method, the balloon is partially inflated and sprayed with a water soluble coating; after which the patch is applied, the balloon is deflated, and the assembly dried.

A water soluble coating of 50 mg/ml of PVP in ethanol was prepared. A 10×40 mm angioplasty balloon was inflated to 4 atm pressure and sprayed with the PVP solution in ethanol. Before the PVP solution dried, a patch prepared as in example 2 above was wrapped around the balloon. The balloon then was deflated and dried. In a second test, a commercial 6×40 mm balloon was unwrapped (from its tight fold) and sprayed with a water soluble coating. A patch prepared as in Example 2 was wrapped around the balloon, and the assembly was dried and folded back again into a tight fold. Alternatively, the patch and balloon may be tightly folded and then dried.

Example 4

Use of a sheath on the exterior of the patch and balloon catheter was investigated to reduce fluid uptake and premature activation of the patch. It is believed to be important that the sheath be sufficiently close fitting to prevent water from penetrating the gap between the patch and the sheath, so as to prevent the patch from becoming activated prematurely and adhering to the sheath. On the other hand, sliding a tightly fitting sheath over the patch could potentially mechanically damage the patch. In addition, other methods may be employed to prevent water from entering the sheath during delivery, such as by providing pillows on the balloon that permit it to be partially inflated to seal the gap between the balloon catheter and sheath.

A patch prepared as described in Example 2 was wrapped around a 10×40 mm balloon prepared as described in Example 3. A sheath having an inner diameter of about 2.5 mm was easily slid over the patch and the balloon so the patch was not damaged. The balloon was then inflated inside of the sheath to about 2 atm pressure to achieve a tight seal between the balloon and the sheath. During delivery, after the balloon is disposed at the deployment site, negative pressure may be applied to the balloon and the sheath slid away. The balloon may then be inflated to deploy the patch.

Example 5

The effect of the balloon size on patch delivery was investigated. It was observed that the ratio of balloon diameter to target lumen diameter plays an important role in successful deployment of the patch. In particular, it was observed that the target lumen needs to be sufficiently large enough so the balloon can travel inside it easily, and without significant friction. The lumen also must be sufficiently large that, after the patch is deployed and the balloon is deflated, the patch is not mechanically damaged, e.g., scratched off, when the balloon is being removed. As a further consideration, the artery or lumen must be sufficiently small that inflation of the balloon inside of the lumen creates enough pressure against the luminal wall that the balloon comes fully in contact with the luminal wall over its entire area. It was observed that a ratio of balloon diameter to target lumen diameter of about 1.1:1 provided good results. Accordingly, a 10 mm balloon is believed to be suitable to deliver a patch inside a 9 mm lumen. In addition, folding of the balloon and ratio of the deflated to inflated size of the balloon can impact the results obtained: it was generally found desirable to have the balloon folded to the smallest diameter attainable without damaging the patch.

A patch wrapped around a 10×40 mm balloon as prepared in Example 3 was expanded inside a plastic tube with an inner diameter of about 9 mm, while the plastic tube was immersed in saline solution. In order to deploy the patch, the balloon was expanded to 8 atm and held at that pressure for 10 seconds before being deflated and removed. In a separate test, a similar tube with a patch deployed inside, as described above, was placed in a flow system with a flow rate of about 1200 ml/min. The patch remained intact for the 48 hour duration of the experiment. By comparison, the flow rate in human superficial femoral artery, a potential target site for deployment of the inventive patch, is about 200 ml/min. Similar tests conducted with beef aorta instead of plastic tubing produced comparable results for patch deployment and durability.

Example 6

Feasibility of use of a patch in accordance with the present invention in a lumen having a side branch was investigated. As discussed above, it is contemplated that a patch constructed in accordance with the present invention could be deployed in a vessel having a side branch, without occluding the side branch. In particular, it is believed that a patch disposed within a target vessel adheres to only those portions of the vessel wall where the patch was brought into apposition by the delivery system. Preferably, the area of the patch facing the side branch opening would remain on the balloon, thus leaving the side branch open.

A patch and delivery system as described in Example 3 was prepared, and the patch was deployed inside a plastic tube having a 3 mm diameter hole drilled on one side of the tube to represent a side branch. After deployment of the patch, the side branch remained open and a 9 mm$^2$ area of the patch was found to have remained on the balloon, corresponding to that portion of the patch that was deployed against the hole.

Example 7

The feasibility of using a patch of the present invention for drug delivery was investigated. The expectation that it is possible to incorporate any therapeutically useful molecule or ingredient in the formulation of the patch as described herein was tested using patch including PEG-400 and a dye. It is contemplated that therapeutic agents can be incorporated in the formulation in a similar fashion. For example, a desired therapeutic molecule may be dissolved or suspended in an organic solvent and added to either the fibrinogen or the thrombin solutions during the preparation of the patch. In this way the molecule will be trapped inside the fibrin structure and will be delivered over time as the fibrin biodegrades.

Red dye was ground and suspended in ethanol in a ratio of 100 mg/ml. A patch was prepared using the formulation of Example 2, except that 40 µl of the color suspension was added to the fibrinogen suspension prior to mixing with the thrombin solution. After drying, the patch was placed in 4 ml of saline solution and monitored at 2 hour intervals. After 4 hours, it was observed that the red dye had been slowly released into the saline solution. Similar release is expected to occur with a therapeutic agent instead of a dye.

Example 8

The feasibility of incorporating a radiopaque material into a patch of the present invention to improve visibility under fluoroscopic imaging was investigated. In order to render the patch radiopaque under fluoroscopy, it is desirable to incorporate a radiopaque material in the patch. The radiopaque material may be non-water soluble, such as barium sulfate, or water soluble, such as iodinated contrast agents. These agents can be added to the patch in the same manner as the red dye was added in Example 7.

Barium sulfate often is added to medical devices, usually in a range of 30 wt %, to render such medical devices radiopaque. It was observed that adding such agents at similar weight ratios (30%) of barium sulfate or iodinated contrast agent (iopromide) did not result in observable radiopacity of the patch. It is believed that this result obtained due to the open structure of fibrinogen and the low density of the patch, which was not sufficiently dense to provide the required degree of radiopacity. It was further observed that much higher quantities of the agents were required to produce an acceptable degree of radiopacity. Surprisingly, however, it was found that a patch as formulated above is capable of incorporating significant quantities of radiopaque materials—in some cases multiples of the weight of the fibrinogen and thrombin components, without deterioration in the integrity of the patch. On the other hand, the flexibility, and therefore deliverability of the patch were significantly affected by incorporation of large amounts of foreign particles.

To resolve the foregoing issue, use of a thin strip of a radiopaque patch (that contains high concentration of radiopaque material) was tested as a marker on a patch that did not otherwise contain contrast agent. This approach makes use of the adhering capability of the patch, which maintains its integrity even in the presence of the contrast agent. The result is a biodegradable radiopaque marker that can be adhered to any medical device, including the patch.

A first radiopaque patch was prepared using the formulation of Example 2, except that 100 mg of barium sulfate was added to the fibrinogen suspension prior to mixing with the thrombin solution. A second patch was prepared using the formulation of Example 7, except that only 20 µl of color suspension was added to the fibrinogen suspension prior to mixing with the thrombin solution. The patches were dried for 3 hours under 30 mm Hg vacuum. A radiopaque marker band was then formed by cutting a rectangular strip having dimensions of 3 mm by 25 mm from the first radiopaque patch. The strip was slightly wetted with water and immediately placed in the middle of a 20 mm by 25 mm rectangular strip of the second patch.

A second radiopaque patch was prepared using the formulation of Example 2, except that 200 mg of iopromide powder was added to the fibrinogen suspension prior to mixing with the thrombin solution. A second patch was prepared using the formulation of Example 7, except that again only 20 µl of color suspension was added to the fibrinogen suspension prior to mixing with the thrombin solution. The patches were dried for 3 hours under 30 mm Hg vacuum. A radiopaque marker band was then formed by cutting a rectangular strip having dimensions of 3 mm by 25 mm from the second radiopaque patch. The strip was slightly wetted with water and immediately placed in the middle of a 20 mm by 25 mm rectangular strip of the second patch.

The two patches prepared above with radiopaque markers were observed under fluoroscope and compared to a bare metal stent. Both patches demonstrated radiopacity comparable to that of the bare metal stent. It was observed that using a non-water soluble contrast agent, such as barium sulfate, in the marker band is advantageous because it has a longer residence time in the marker. Thus, barium sulfate will not dissolve in blood and therefore should remain in the marker for a longer period of time. Over time, the barium sulfate is expected to diffuse out of the fibrin network or be released upon absorption of the fibrin, and then washed away with the blood stream. Iopromide, on the other hand, is water soluble and will dissolve in blood contacting the fibrin matrix. Based on the tests conducted, it is expected that the iopromide patch will lose its radiopacity within 72 hours, while the barium sulfate marker band is expected to persist for a longer interval.

While various illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. A device comprising:
   a film comprising a mixture of solid fibrinogen and solid thrombin,
   wherein the film is free-standing and is configured to form a fibrin patch upon exposure to moisture, and
   wherein the film further comprises a plasticizer that comprises about 5 to about 30 weight percent polyethylene glycol.

2. The device of claim 1, wherein the solid fibrinogen is prepared from unsalted fibrinogen.

3. The device of claim 1, wherein the film further comprises calcium salt.

4. The device of claim 1, wherein the film further comprises a therapeutic agent, and wherein the fibrin patch is configured to release the therapeutic agent.

5. The device of claim 4, wherein the therapeutic agent comprises one or more anti-inflammatory agents, anti-allergenic agents, anti-bacterial agents, anti-viral agents, anticholinergic agents, antihistamines, antithrombotic agents, anti-scarring agents, antiproliferative agents, antihypertensive agents, anti-restenosis agents, healing promoting agents, vitamins, proteins, genes, growth factors, cells or DNA.

6. The device of claim 1, wherein the polyethylene glycol comprises PEG 400, PEG 1500, PEG 3000, or PEG 6000.

7. The device of claim 1, wherein the film further comprises a contrast agent that renders the device radiopaque.

8. The device of claim 7, wherein the contrast agent is concentrated in a marker band region comprised of a mixture of solid fibrinogen and solid thrombin.

9. The device of claim 1, wherein the film is coated with a water-soluble protective layer.

10. The device of claim 1, wherein the film comprises two or more layers of solid fibrinogen and solid thrombin.

11. The device of claim 9, wherein at least one of the two or more layers contains relative amounts of solid fibrinogen and solid thrombin different than others of the two or more layers.

12. The device of claim 1, wherein the device comprises a patch that is non-adherent prior to exposure to moisture.

13. The device of claim 1, wherein the device comprises a patch that is adherent prior to exposure to moisture.

14. A device comprising:
    a film comprising a mixture of solid fibrinogen and solid thrombin, wherein the film is free-standing and is configured to form a fibrin patch upon exposure to moisture, and wherein the solid fibrinogen is prepared from unsalted fibrinogen.

15. A device comprising:

a film comprising a mixture of solid fibrinogen and solid thrombin, wherein the film is free-standing and is configured to form a fibrin patch upon exposure to moisture, and wherein the film further comprises a contrast agent that renders the device radiopaque.

16. The device of claim 15, wherein the contrast agent is concentrated in a marker band region comprised of a mixture of solid fibrinogen and solid thrombin.

* * * * *